United States Patent [19]
Jernberg

[11] Patent Number: 5,939,047
[45] Date of Patent: Aug. 17, 1999

[54] LOCAL DELIVERY OF CHEMOTHERAPEUTIC AGENTS FOR TREATMENT OF PERIODONTAL DISEASE

[76] Inventor: Gary R. Jernberg, 2283 Northridge Dr., North Mankato, Minn. 56003

[21] Appl. No.: 08/633,152

[22] Filed: Apr. 16, 1996

[51] Int. Cl.$^6$ .............................. A61K 9/50; A61K 9/62; A61K 31/725

[52] U.S. Cl. .............................. 424/49; 514/54; 514/900; 514/902; 514/963; 424/489; 424/493

[58] Field of Search ........................... 424/49, 489, 493; 514/54, 900, 902

[56] References Cited

U.S. PATENT DOCUMENTS

| | | | |
|---|---|---|---|
| 4,636,524 | 1/1987 | Balazs et al. | 514/781 |
| 4,685,883 | 8/1987 | Jernberg . | |
| 4,736,024 | 4/1988 | della Valle et al. | 536/55.3 |
| 4,764,377 | 8/1988 | Goodson | 424/435 |
| 4,780,320 | 10/1988 | Baker | 424/493 |
| 4,851,521 | 7/1989 | della Valle et al. | 536/55.1 |
| 4,919,939 | 4/1990 | Baker | 424/493 |
| 4,937,254 | 6/1990 | Sheffield et al. | 514/420 |
| 4,957,744 | 9/1990 | Della Valle et al. | 424/401 |
| 5,059,123 | 10/1991 | Jernberg, II | 433/215 |
| 5,095,037 | 3/1992 | Iwamitsu et al. | 514/561 |
| 5,110,720 | 5/1992 | Csányi et al. . | |
| 5,166,331 | 11/1992 | Della Valle et al. | 536/55.1 |
| 5,197,882 | 3/1993 | Jernberg, III | 433/215 |
| 5,202,431 | 4/1993 | Della Valle et al. | 536/55.1 |
| 5,290,271 | 3/1994 | Jernberg, IV | 604/891.1 |
| 5,336,767 | 8/1994 | Della Valle et al. | 536/55.1 |
| 5,447,940 | 9/1995 | Harvey et al. . | |
| 5,536,508 | 7/1996 | Canal et al. | 424/501 |
| 5,626,838 | 5/1997 | Cavanaugh | 424/54 |
| 5,639,738 | 6/1997 | Falk et al. | 514/54 |
| 5,644,049 | 7/1997 | Givsti et al. | 536/53 |
| 5,646,129 | 7/1997 | Callegaro et al. | 514/54 |

FOREIGN PATENT DOCUMENTS

| | | |
|---|---|---|
| WO 91/04058 | 4/1991 | WIPO . |
| WO 93/16732 | 9/1993 | WIPO . |
| WO 93/16733 | 9/1993 | WIPO . |
| WO 94/07505 | 3/1994 | WIPO . |

OTHER PUBLICATIONS

Rajedhyaksha, V.J., et al. "Oxazolidinones: Optimizing Delivery of Active Ingredients in Skin Care Products", *Drug & Cosmetic Industry* (Mar. 1996).

Brown, M.B., et al., "A study of the transdermal grug delivery properties of hyaluronan", *Third International Workshop on Hyaluronan in Drug Delivery, Royal Society of Medicine Press Ltd.* (1995).

Bennett, F.C., et al., "The diffusion of diclofenac from hyaluronan and other polysaccharide formulations through human skin in vitro", *Fourth International Workshop on Hyaluronan in Drug Delivery, Royal Society of Medicine Press Ltd.* (1996).

Lin, W., et al., "Percutaneous absorption of diclofenac in hyaluronic acid gel: in vitro study in human skin", *Fourth International Workshop on Hyaluronan in Drug Delivery, Royal Society of Medicine Press Ltd.* (1996).

El Attar, et al. "Arachidonic acid metabolism in inflammed gingiva and its inhibition by anti–inflammatory drugs", *J. Periodontol* 1984; 55:536–539.

Feldman, et al., "Nonsteriodal anti–inflammatory drugs in the reduction of human alveolar bone loss", *J. Periodontol* 1983, 10:131–136.

Genco, "Antibiotics in the treatment of human peridontal diseases", *J. Periodontol* 1981, 52:545–558.

Golub, et al., Tetracyclines inhibit tissues collagenase activity, *J. Periodont Res.* 1984, 19:651–655.

Golub, et al., "Tetracyclines inhibit tissue collagenase. Effects of ingested low–dose and local delivery systems", *J. Periodontol* 1985, 56 (Suppl.):93–97.

Goodson, "A Potential role of prostaglandins in the etiology of periodontal disease", *Protaglandins and cyclic AMP*, Academic Press, New York, 1973, pp. 215–216.

Goodson, et al., "Periodontal therapy by local delivery of tetracycline", *J. Clin Periodontol* 1979; 6:83–92.

Kakehasi, et al., "Proceedings fro mthe state of the art workshop on surgical therapy for peridontitis", *J. Periodontol* 1982: 53:475–501.

Lewis, et al., "Nonsteriodal anti–imflammatory drugs in periodontal disease", *NSAIDS in Periodontal Disease*, Marcel Dekker, Inc., New York, 1987, pp. 143–155.

Lindhe, et al., "Local tetracycline delivery using hollow fiber devices in periodontal therapy", *J. Clin Periodontol* 1979; 6:141–149.

Page, et al., *Periodontol Disease*, Chapter 8, "Pathogenic Mechanisms", Lea and Febiger, Philadelphia, 1989, pp. 221–261.

Vogel, et al., The effects of topical steriodal and systemic nonsteriodal anti–inflammatory drugs on experimental gingivitis in man:, *J. Periodontol* 1984; 55:247–251.

Waite, et al., "The periodontal status of subjects receiving nonsteriodal anti–inflammatory drugs", *J. Periodont res.* 1981; 10:90–100.

Weeks–Dybrig, et al., "The effect of indomethacin on alveolar bone loss in experimental periodontitis", *J. Periodont Res.* 1982; 17:90–100.

Williams, et al., "Topical flurbiprofen treatment of periodontitis in beagles", *J. Periodont Res.* 1988; 23:166–169.

Williams, et al., "Altering the progression of human alveolar bone loss with the nonsteriodal anti–inflammatory drug flurbiprofen", *J. Periodontol* 1989; 60:485–490.

Williams, et al., "Host modulation in the management of periodontal diseases", *Amer. Acad. Periodontol* Apr. 1990 (7 pgs.).

*Primary Examiner*—Shep K. Rose
*Attorney, Agent, or Firm*—Merchant, Gould, Smith, Edell, Welter & Schmidt, P.A.

[57] ABSTRACT

Compositions and methods for treating periodontal disease and other related disorders utilizing a therapeutic treatment composition, including at lease one chemotherapeutic agent in combination with at least one carrier agent, are disclosed. Oral care products and a method preventing periodontal disease and related disorders are also provided.

14 Claims, 2 Drawing Sheets

LOCAL DELIVERY OF CHEMOTHERAPEUTIC AGENTS FOR TREATMENT OF PERIODONTAL DISEASE

TECHNICAL FIELD OF THE INVENTION

The present invention relates to compositions and methods of preventing and treating periodontal disease and related disorders utilizing a sustained, controlled release topical delivery method to optimize the delivery of chemotherapeutic agents to periodontal treatment sites.

BACKGROUND OF THE INVENTION

Periodontal diseases are a major dental affliction to mankind. Gingivitis, inflammation of gingival (gum) tissue, and periodontitis, inflammation and progressive loss of ligament and alveolar (socket) bone support to teeth are caused by bacteria which colonize tooth surfaces and occupy the gingival crevice area. These are the major periodontal disease afflictions worldwide. Bacterial plaque is the principal causative agent of these periodontal diseases. Autoimmune disorders such as desquamative gingivitis and lichen planus comprise another type of periodontal disease resulting in inflamed, sensitive and sometimes ulcerated gingival tissues.

Routine daily prevention or removal of plaque by the patient is a sine qua non in periodontal therapy. This involves the use of toothbrushes, dental floss and various other oral hygiene instruments. These devices require motor skill and dexterity. The daily routines for adequate plaque removal require the patient to be diligent, motivated, educated and skillful. Accordingly, such methods are effective only when used by motivated individuals and then often to a limited extent.

Optimal response of the immune system to defend against bacterial assault is often not realized in patients prone to gingivitis and periodontitis and may actually contribute to the disease process. An improper immune system reaction is responsible for autoimmune periodontal disorders Such as lichen planus and desquamative gingivitis.

Conventional periodontal therapy has emphasized mechanical removal of soft and hard accretions of bacteria (i.e., plaque and calculus) from the root surface via use of dental instruments placed into the gingival crevice to mechanically shear the accretions from the tooth structure. See S. Kakehashi and P. F. Parakkal, *Proceedings from the State of Art Workshop on Surgical Therapy for Periodontitis*, J. Periodontol 53:475 (1982).

Systemic agents have been used in periodontal therapy. See R. J. Genco, *Antibiotics in the Treatment of Human Periodontal Diseases*, J. Periodontol 52:545 (1981). However, systemic delivery (e.g., oral or intramuscular) often does not provide a strong enough concentration of chemotherapeutic agent over an extended period of time to the specific area where required. This is of particular concern with regard to the gingival crevice. In addition, the possibility exists that indigenous bacteria may develop resistance to such a method of delivery of antibiotic.

Recent studies have focused on the use of the local delivery of tetracycline to periodontal lesions via non-degradable fibers placed into the lesion with dental instruments. This method has shown promise in transient elimination or control of localized subgingival bacteria. See J. M. Goodson, A. Haffajee and S. S. Socransky, *Periodohtol Therapy by Local Delivery of Tetracycline*, J. Clin Periodontol 6:83 (1979); and J. Lindhe, et al, *Local Tetracycline Delivery Using Hollow Fiber Devices in Periodontal Therapy*, J. Clin Periodontol 6:141 (1979). However, a problem with this method is that the non-degradable fibers must be removed after treatment. Also, the locally applied method may not deliver an adequate, sustained quantity of tetracycline to the soft tissues of the treatment site. Furthermore, the fiber is subsequently removed after ten days and the delivery of tetracycline is depleted.

Applicant's U.S. Pat. No. 4,685,883 deals with controlled, sustained release of chemotherapeutic agents in a bioerodable matrix in the periodontal lesion via placement of the matrix into the lesion with dental instruments. In one embodiment, the chemotherapeutic agents are incorporated into microspheres. As with the method described by Goodson et al., Applicant's previous method may not deliver an adequate, sustained quantity of chemotherapeutic agents to the tissues proximate the treatment site.

Although specific bacteria are essential agents for many periodontal diseases, their presence alone on the tooth surface and underneath the gingiva is not sufficient to explain the periodontal disease process. Rather, the host must react to these inciting agents if disease is to develop and progress. As with other bacterial infections, the host's immune system localizes at the invasion site and attempts rapidly to neutralize, remove, or destroy the bacterial agents. In periodontal disease, however, chronic bacterial plaque accumulation causes an excessive and persistent antigenic stimulus. Therefore, the host response, rather than being protective and self-limiting, can be destructive. See R. C. Page, *Periodontal Disease*, p.221, Lea and Febiger, Philadelphia, 1989.

The ability to modulate or block specific cellular and humoral factors involved in the disease process could lead to new and more effective prevention and treatment methods as adjuncts in the management of periodontal diseases. At the present, two host responses which are considered important in periodontal tissue destruction have the potential to be modulated or blocked with pharmacologic agents. Blocking of these host pathways should have an impact on periodontal disease progression. The first host response involves the cyclooxygenase pathway products of arachidonic acid metabolism. The second involves collagenolysis of periodontal structures via gingival collagenase. See R. C. Williams, *Host Modulation in the Management of Periodontal Diseases*, pp. 1–3, American Academy of Periodontology, Department of Scientific Clinical and Educational Affairs, Chicago, 1990.

Studies utilizing nonsteroidal anti-inflammatory drugs for treatment of gingivitis and periodontitis have yielded potential promise for controlling the progression of these diseases. See Alan J. Lewis and Daniel E. Furst, *Nonsteroidal Anti-inflammatory Drugs, Mechanisms and Clinical Usd*, pp. 143–155, Marcel Dekker, Inc., New York, 1987. Nonsteroidal anti-inflammatory drugs (NSAIDS) inhibit the production of prostaglandins and other deleterious metabolic products from arachidonic acid in the cyclooxygenase pathway. There is strong evidence to suggest that cyclooxygenase pathway products of arachidonic acid, such as prostaglandins, may be important biochemical mediators of some of the pathological events of periodontal disease, such as gingival inflammation and bone resorption. Waite and co-workers reported that patients taking NSAIDS for arthritis or ankylosing spondylitis has a lower gingival index and shallower periodontal pockets than individuals not taking NSAIDS. See I. M. Waite, et al, *The Periodontal Status of Subjects receiving Non-Steroidal Anti-Inflammatory Drugs*, J. Periodont Res 16:100 (1981). Williams, et al studied the effect of the NSAID flurbiprofen on slowing alveolar bone loss in humans. Flurbiprofen administered 50 mg. p.o. twice daily significantly inhibited the radiographic loss of alveolar bone compared to placebo-treated patients for up to eighteen months. See R. C. Williams, et al, *Altering the Progression of Human Alveolar Bone Loss with the Non-Steroidal Anti-Inflammatory Drug Flurbiprofen*, J. Periodontol 60:485 (1989).

Golub and co-workers have presented evidence that tetracycline and semi-synthetic analogues minocycline and doxycycline can directly inhibit the activity of collagenolytic enzymes such as mammalian collegenase. A chemically-modified tetracycline, with no antibiotic efficacy, was also found to inhibit collagenase activity. See L. M. Golub, et al, *A Non-Antibacterial Chemically Modified Tetracycline Inhibits Mammalian Collagenase Activity*, J. Den Res 66:1310 (1987).

Inadequate concentrations of chemotherapeutic agents at the intended periodontal treatment site are often achieved with oral dosing (e.g., tablets or capsules for ingestion) for systemic distribution. Moreover, deleterious side effects often occur (e.g., gastrointestinal problems with long term NSAID administration). Also, variability of concentration over time is a problem. Peaks and valleys of agent concentration are noted over time relative to the dosing interval.

A lack of sustained, controlled delivery is found with conventional topical delivery of chemotherapeutic agents to periodontal sites. Diminished concentration occurs rapidly in most instances with topically applied gels, pastes or mouthrinses. An exception to this are the antimicrobial mouthrinses comprising chlorhexidine gluconate which bind externally to teeth and gingival tissues. The mouthrinse delivery does not allow for substantial penetration into the gingival tissues or periodontal pocket, however, and therefore these agents are not effective as mouthrinses against periodontitis because they do not target the periodontal pocket. Furthermore, irrigations into the periodontal pocket are not very effective as they are rather quickly swept away by normal outward gingival crevicular flow. Previously studied mouthrinses containing NSAIDS can penetrate gingival tissues and ultimately travel to the intended site but not at a continuously sustained concentration to yield sufficient efficacy to warrant their use on a continuous, long term basis.

The present invention solves these and other problems by optimizing the availability of chemotherapeutic agents at the localized periodontal treatment site by utilizing the periodontal soft tissues as a reservoir for the chemotherapeutic agents thereby providing for adequate, sustained and controlled delivery of the chemotherapeutic agents to the appropriate cells of the periodontal tissues to favorably modulate the host immune response. This also reduces the overall exposure to the chemotherapeutic agents by lowering the necessary dosing along with eliminating exposure to the chemotherapeutic agents at unnecessary sites.

SUMMARY OF THE INVENTION

The present invention relates to the compositions and methods providing for the delivery of chemotherapeutic agents to localized sites in the mouth, via deposition into the periodontal tissues, for sustained, controlled, targeted release in the prevention and treatment of periodontal disease.

In one embodiment of the present invention, a method of treating periodontal disease is provided whereby at least one chemotherapeutic agent is combined with at least one carrier agent to form a therapeutic treatment composition which is applied to diseased gingival tissues at a localized periodontal site.

In another embodiment of the present invention, a method of preventing periodontal disease is provided whereby at least one chemotherapeutic agent in combination with at least one carrier agent is periodically applied to the gingival tissues to prevent periodontal disease and other related disorders.

In yet another embodiment of the present invention, a therapeutic treatment composition composed of at least one chemotherapeutic agent combined with at least one carrier agent is provided.

In still another embodiment of the present invention, various oral care products incorporating at least one chemotherapeutic agent combined with at least one carrier agent are provided. Examples would include, but not be limited to, toothpastes, mouthrinses, periodontal pocket locally applied gels, or swab or toothbrush applied viscid liquids, or gels or pastes.

In all the embodiments of the compositions and methods of present invention, the carrier agent increases the tissue uptake of the chemotherapeutic agent relative to compositions and methods lacking in the carrier agent.

These and various other advantages and features of novelty which characterize the invention are pointed out with particularity in the claims annexed hereto and forming a part hereof. However, for a better understanding of the invention, its advantages, and objects attained by its use, reference should be made to the drawings which form a further part hereof, and to the accompanying descriptive matter, in which there is illustrated and described preferred embodiments of the invention.

BRIEF DESCRIPTION OF THE DRAWINGS

In the drawings, in which like reference numerals and letters indicate corresponding parts throughout the several views.

DETAILED DESCRIPTION OF THE INVENTION

Figure 1A:
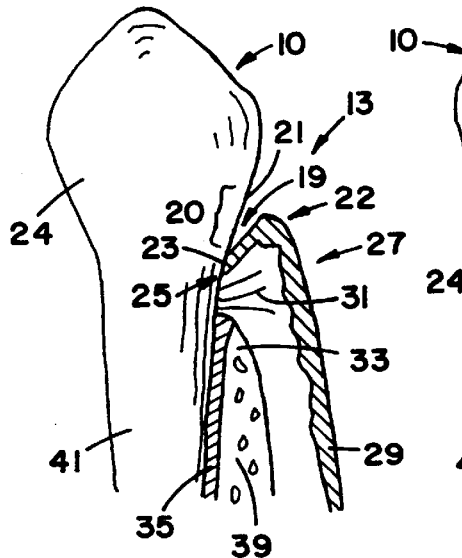
FIGS. 1A through 1C are diagrammatic views illustrating the human periodontal anatomy, including an illustration of the healthy human periodontium in FIG. 1A, an illustration of the effects of gingivitis in FIG. 1B, and an illustration of the effects of periodontitis in FIG. 1C.
Figure 1B:
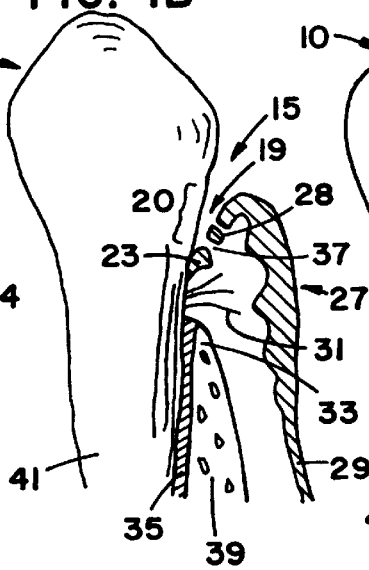
Figure 1C:
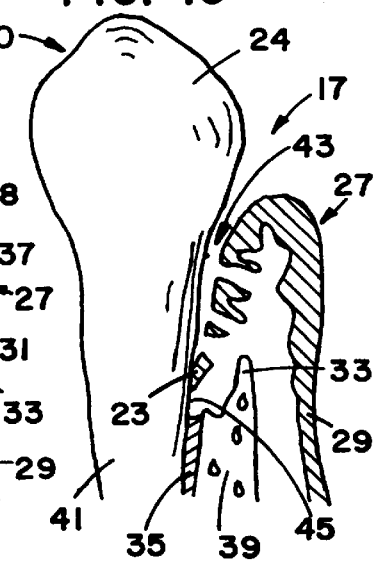
Figure 2:
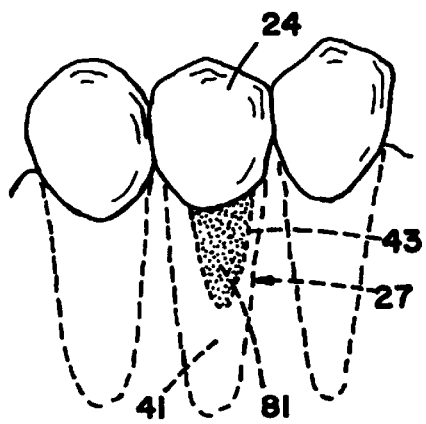
FIG. 2 is a partial diagrammatic view illustrating the placement into a periodontal pocket lesion, between the tooth and gingival tissue, of a gel or paste.

Referring now to FIGS. 1A through 1C, wherein there is diagrammatically illustrated a human periodontal anatomy 10, progressing from a healthy human periodontium 13 illustrated in FIG. 1A to a periodontium inflicted with periodontitis 17 illustrated in FIG. 1C.

Specifically, FIG. 1A illustrates a healthy human periodontium 13. Between the gingival margin 21 and the free gingiva 22 is the healthy gingival suldus or crevice 19. The depth 20 of the gingival sulcus or crevice 19, from the gingival margin 21 to the attachment of the junctional epithelium 23, is approximately 1–3 millimeters. The junctional epithelium attaches to the tooth 24 at the cementoenamel junction (CEJ) 25. The gingival tissues 27, including the epithelium 29 and gingival fibers 31, are healthy and without inflammation. The alveolar bone crest 33 and periodontal ligament 35 are undamaged.

FIG. 1B illustrates the human periodontium 10 inflicted with gingivitis 15. The gingival tissues 27 show signs of inflammation and crevicular ulceration 37, resulting in white cell infiltration into the gingival sulcus or crevice 19. Furthermore, the ulcerations 37 in the crevicular epithelium 28 results in bleeding upon provocation, such as through brushing and/or flossing of the teeth and gums.

FIG. 1C illustrates the human periodontium inflicted with periodontitig 17. The gingival tissues 27 are inflamed. The alveolar bone crest 33 and periodontal ligament 35 have broken down due to both bacterial and host defense factors. The breakdown of the attachment of the alveolar bone 39 and periodontal ligament 35 to the tooth root 41 has resulted in the formation of a periodontal pocket lesion 43. In addition, apical proliferation of the junctional epithelium 23 is noted along the root surface 45. A chronic white cell infiltrate in the periodontal pocket lesion 43 is persistent. If left untreated, the continual loss of alveolar bone tissue 39 would result in the loss of the tooth 24.

Accordingly, the present invention provides methods and compositions for the treatment and prevention of periodontal disease. Specifically, in a first aspect, the present invention provides a method of treating periodontal disease comprising combining at least one chemotherapeutic agent with at least one carrier agent to form a therapeutic treatment composition and applying the therapeutic treatment composition to a localized periodontal treatment site, wherein the carrier agent increases the deposition and retention of the chemotherapeutic agent in the periodontal tissues at the localized periodontal treatment site relative to a therapeutic treatment composition lacking in the carrier agent.

In a second aspect, the present invention provides a method of preventing or treating periodontal disease comprising periodically applying a therapeutic treatment composition to the gingival tissues of a human or mammal, wherein the therapeutic treatment composition includes an effective amount of at least one chemotherapeutic agent in combination with an effective amount of at least one carrier agent, and further wherein the carrier agent increases the deposition and retention of the chemotherapeutic agent by the gingival tissues relative to a therapeutic treatment composition lacking in the carrier agent.

In a third aspect, the present invention also provides a therapeutic treatment composition effective to treat periodontal disease. The therapeutic treatment composition is comprised of an effective amount of at least one chemotherapeutic agent and an effective amount of at least one carrier agent. The combination of the carrier agent with the chemotherapeutic agent in the therapeutic treatment composition increases the deposition and retention of the chemotherapeutic agent in the periodontal tissues at a localized periodontal treatment site relative to a therapeutic treatment composition lacking in the carrier agent.

In a fourth aspect, the present invention provides an oral care product effective to prevent periodontal disease comprising an effective amount of at least one chemotherapeutic agent and an effective amount of at least one carrier agent, wherein the carrier agent increases the deposition and retention of the chemotherapeutic agent in the periodontal tissues at a localized periodontal treatment site relative to an oral care product lacking in the carrier agent, and further wherein the periodic application of the oral care product to the gingival tissues or oral mucosa of a human or mammal is effective to prevent periodontal disease.

A variety of chemotherapeutic agents can be utilized in the compositions and methods of the present invention. For example, non-steroidal anti-inflammatory agents such as, ibuprofen and anticollagenase agents such as chemically modified tetracycline may be employed, depending upon the particular treatment or preventative goals sought. As used herein, chemotherapeutic agent is meant to include any agent which has biological or physiological activity with respect to the host modulation of periodontal disease and other related disorders.

Anti-inflammatory agents are divided into steroidal and nonsteroidal anti-inflammatory agents. Preferred steroidal anti-inflammatory agents include cortisone, hydrocortisone, beta-methasone, dexamethasone and prednisolone. Preferred nonsteroidal anti-inflammatory agents include indomethacin, flurbiprofen, meclofenamic acid, ibuprofen, naproxen and diclofenac.

As used herein, carrier agent specifically refers to any agent which increases the deposition and retention of the chemotherapeutic agent of the therapeutic treatment compositions and oral care products according to the compositions and methods of the present invention by the tissue or other cells proximate the localized periodontal treatment site. Thus, it will be appreciated that other substances such as diluents, solvents, fillers, flavorings, stabilizers or other ingredients utilized to facilitate the combination, handling or other properties of the therapeutic treatment compositions and/or oral care products, and which do not exhibit the effect of increasing the tissue deposition and retention of the chemotherapeutic agent, are not considered as carrier agents for the purpose of the present invention. While applicant does not wish to be held to a mode of action for the carrier agent in increasing the cellular uptake of the associated chemotherapeutic agent, it is believed that the carrier agent acts upon the periodontal soft tissues to enable penetration through or between cells into the tissue mass and allow for deposition and retention in the tissues so as to facilitate the transport of the chemotherapeutic agent to the desired cells types. Also, the carrier agent may act to better penetrate a tissue mass via enhanced movement of chemotherapeutic agents through the vasculature.

The therapeutic treatment compositions and/or oral care products may be derived by physically mixing a chemotherapeutic agent and a carrier agent together or by chemically linking them by esterification, for example.

Preferred carrier agents include, without limitation, hyaluronic acid, salts thereof such as sodium hyaluronate, esters, enzymatic derivatives and cross-linked gels of hyaluronic acid and chemically modified derivatives of hyaluronic acid such as hylan. As used herein, hyaluronic acid broadly refers to naturally occurring, microbial and synthetic derivatives of acidic polysaccharides of various molecular weights constituted by residues of D-glucuronic acid and N-acetyl-D-glucosamine.

It will be appreciated that the therapeutic treatment compositions and oral care products according to the compositions and methods of the present invention can occur in any form depending upon their intended mode of delivery and the inactive substances, such as fillers or flavorings, associated therewith. Specifically, the therapeutic treatment compositions and oral care products may occur in a solid form, a semi solid form (e.g., gel, paste or viscid liquid), a liquid form or combinations thereof. For example, in certain applications the therapeutic treatment compositions and oral care products can be comprised of a chemotherapeutic agent formed as a solid microparticulate interspersed in a gel comprising the carrier agent, while in other applications both agents may appear in solution. In addition, it will be further appreciated that all other variations on the forms, including combinations thereof, of the therapeutic treatment compositions and oral care products according to the present invention are considered to fall within the scope of the present invention. Thus, in one embodiment, the therapeutic treatment composition and/or oral care product according to the compositions and methods of the present invention is incorporated into a solution comprising a mouthrinse. In such an embodiment, the therapeutic treatment composition and/or oral care product is topically delivered to the gingival tissues by rinsing of the mouth.

In a second embodiment, the therapeutic treatment composition and/or oral care product according to the compositions and methods of the present invention is incorporated into a viscid liquid, gel or paste. These compositions can then be directly applied to the gingival tissues or oral mucosa. As illustrated in FIG. 3B, a preferred means for such delivery may include a swab 90 utilized to topically apply the therapeutic treatment composition and/or oral care product to the gingival tissues 27. Additional means of delivering the compositions may include, without limitation, a cotton ball, or direct application with a finger.

Figure 3A:
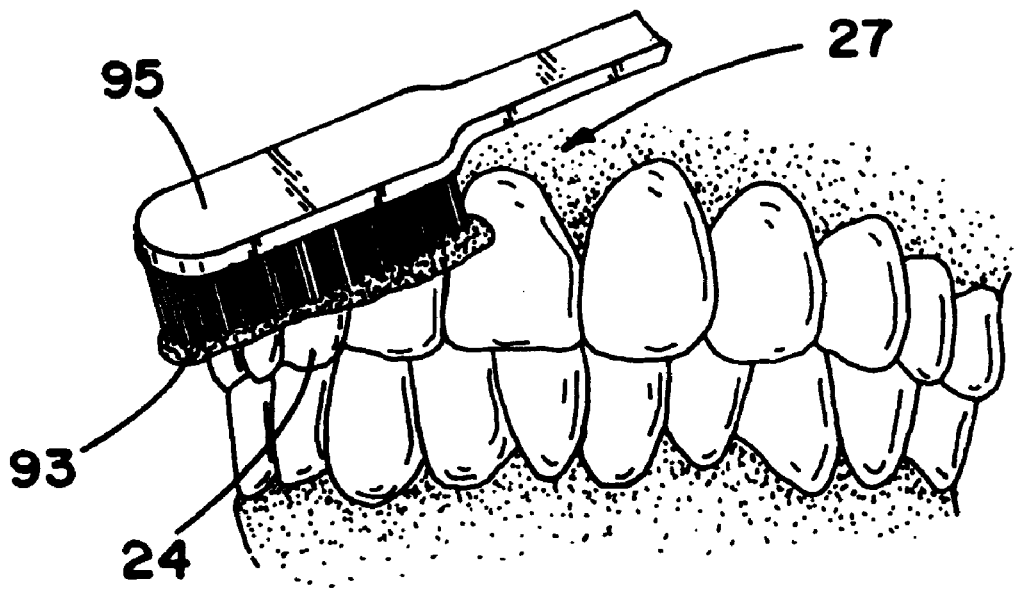
FIGS. 3A and 3B are illustrations of alternative embodiments of topically delivering the therapeutic treatment compositions according to the present invention to the gingival tissues of a human mouth, including delivery of a paste, gel or viscid liquid by a toothbrush in FIG. 3A or a swab in FIG. 3B.
Figure 3B:
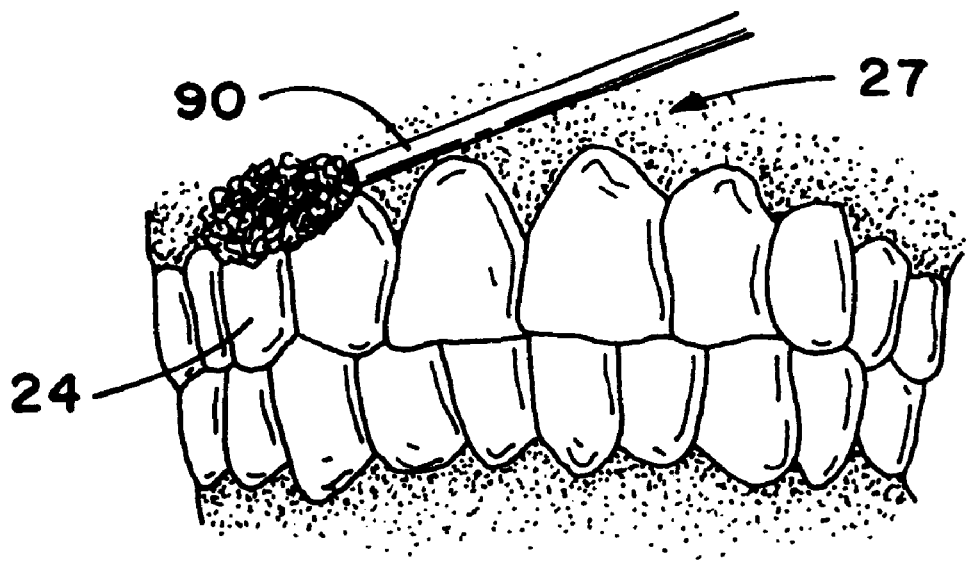

As illustrated in FIG. 3A, in a particularly preferred embodiment, the therapeutic treatment composition and/or oral care product according to the compositions and methods of the present invention is incorporated into a gel or toothpaste 93 and topically applied to the teeth 24 and gingival tissues 27 with a toothbrush 95. Such a method of delivery is particularly preferred, as most patients are familiar with the action of brushing their teeth with toothpaste. Accordingly, these patients can easily incorporate application of the therapeutic treatment compositions and/or oral care products according to the present invention into a consistent, daily treatment or preventative program for periodontal disease and other related disorders.

It will be appreciated that the oral care products and methods of prevention of the present invention can be directed towards the prevention of periodontal disease as well as the treatment of a pathological occurrence of periodontitis, gingivitis or other related disorders. Thus, in accordance with the preventive goals sought, the oral care products according to the present invention incorporate optimal dosages of the chemotherapeutic and carrier agents effective to inhibit the occurrence of periodontal disease prior to degradation of the gingival tissues, alveolar bone crest and/or periodontal ligament. Furthermore, the oral care products and methods are formulated and designed for periodic application to the gingival tissues, preferably on a daily basis. Also, it will be appreciated that formulations may be adopted which are particularly useful for preventing the reoccurrence of periodontal disease in those patients previously successfully treated for periodontal disease and other related disorders.

If the chemotherapeutic agent is present in a solid form, then microspheres between 10 and 700 microns in diameter are preferred. Various chemical and physical methods for preparing microspheres and other microshapes have been developed over the past twenty-five years and are well known to those skilled in the art. In this regard, see for example Patrick B. Deasy, *Microencapsulation and Related Drug Processes*. Marcel Dekker Inc., New York, 1984.

Coacervation, interfacial polymerization, solvent evaporation and spray drying are examples of methods used in the production of microspheres which are capable of incorporating the therapeutic treatment compositions of the present invention. For example, the microencapsulated therapeutic treatment compositions can be incorporated into a gel, paste or toothpaste 93, such as illustrated in FIGS. 3A and 3B, and topically applied with a swab 90 or toothbrush 95.

It will be further appreciated that the particular chemotherapeutic agents and carrier agents comprising the therapeutic treatment compositions and oral care products of the compositions and methods of the present invention, as well as the dosages and durations of treatment will be in accordance with accepted treatment.

It is to be understood, however, that even though numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention, to the full extent indicated by the broad general meaning of the terms in which the appended claims are expressed.

I claim:

1. A method of treating periodontal disease comprising the steps of:

combining at least one chemotherapeutic agent with at least one carrier agent to form a therapeutic treatment composition that is a semi-solid, a liquid, a gel, a paste, a viscid liquid, a mouthrinse, or in a combination of these forms; the chemotherapeutic agent being in microspheres between 10 and 700 microns in diameter; the carrier agent comprising hyaluronic acid, a salt of hyaluronic acid, an ester of hyaluronic acid, an enzymatic derivative of hyaluronic acid, a cross-linked gel of hyaluronic acid, a chemically modified derivative of hyaluronic acid, or a combination thereof; and applying the therapeutic treatment composition to a periodontal treatment site by rinsing, toothbrushing, or swabbing, wherein the carrier agent increases the tissue deposition and retention of the chemotherapeutic agent at the periodontal treatment site relative to the therapeutic treatment composition lacking the carrier agent.

2. A method according to claim 1 wherein the combining step includes selecting the chemotherapeutic agent from the group consisting of anti-inflammatory and anticollagenolytic agents.

3. A method according to claim 2 wherein the combining step includes selecting the anti-inflammatory agent from the group consisting of steroidal anti-inflammatory agents and nonsteroidal anti-inflammatory agents.

4. A method according to claim 3 wherein the combining step includes selecting the non-steroidal anti-inflammatory agent from the group consisting of indomethacin, flurbiprofen, meclofenamic acid, ibuprofen, diclofenac and naproxen.

5. A method according to claim 1 wherein the configuring step includes encapsulating at least one of the chemotherapeutic agents and carrier agents of the therapeutic treatment composition in to the microspheres.

6. A method according to claim 5, wherein the encapsulating step includes selecting microspheres which have time release values, thereby assuring generally continuous release of the therapeutic treatment composition over a predetermined period of time.

7. A method according to claim 6 wherein the configuring step includes mixing at least one of the chemotherapeutic agents and carrier agents of the therapeutic treatment composition with a polymer comprising the microsphere.

8. A method according to claim 5 wherein the carrier agent and/or carrier agent linked chemically to the chemotherapeutic agent is the polymer comprising the microspheres.

9. A method according to claim 7 wherein the polymer is selected from the group consisting of lactic glycolic acid polymers and esters of hyaluronic acid.

10. A method according to claim 1 including the steps of intermixing the microspheres incorporating the therapeutic treatment composition with a viscid liquid, a gel or a paste, and topically applying the admixture to the gingival tissues or oral mucosa.

11. A therapeutic treatment composition effective to treat periodontal disease comprising:

an effective amount of at least one chemotherapeutic agent; the chemotherapeutic agent being in microspheres between 10 and 700 microns in diameter; and an effective amount of at least one carrier agent, wherein, the carrier agent increases the tissue deposition and retention of the chemotherapeutic agent at a periodontal treatment site relative to a therapeutic treatment composition lacking the carrier agent; the carrier agent comprising hyaluronic acid, a salt of hyaluronic acid, an ester of hyaluronic acid, an enzymatic derivative of hyaluronic acid, a cross-linked gel of hyaluronic acid, a chemically modified derivative of hyaluronic acid, or a combination thereof;

wherein the therapeutic treatment composition is in the form of a semi-solid, a liquid, a gel, a paste, a viscid liquid, a mouthrinse or in a combination of these forms, suitable for applying to a periodontal treatment site rinsing, toothbrushing, or swabbing.

12. A method of preventing periodontal disease comprising periodically applying a therapeutic treatment composition in the form of a semi-solid, a liquid, a gel, a paste, a viscid liquid, a mouthrinse or in a combination of these forms by rinsing, toothbrushiing, or swabbing to the gingival tissues or oral mucosa of a human or mammal, wherein the therapeutic treatment composition includes an effective amount of at least one chemotherapeutic agent in combination with an effective amount of at least one carrier agent, and further wherein the carrier agent increases the tissue deposition and retention of the chemotherapeutic agent at the periodontal treatment site relative to the therapeutic treatment composition lacking the carrier agent; the chemotherapeutic agent being in microspheres between 10 and 700 microns in diameter; the carrier agent comprising hyaluronic acid, a salt of hyaluronic acid, an ester of hyaluronic acid, an enzymatic derivative of hyaluronic acid, a cross-linked gel of hyaluronic acid, a chemically modified derivative of hyaluronic acid, or a combination thereof.

13. An oral care product effective to prevent periodontal disease comprising:

an effective amount of at least one chemotherapeutic agent; the chemotherapeutic agent being in microspheres between 10 and 700 microns in diameter; and an effective amount of at least one carrier agent, wherein the carrier agent increases the tissue deposition and retention of the chemotherapeutic agent at a periodontal treatment site relative to the therapeutic treatment composition lacking the carrier agent, and further wherein the periodic application of the oral care product to the gingival tissues or oral mucosa of a human or mammal is effective to prevent periodontal disease; the carrier agent comprising hyaluronic acid, a salt of hyaluronic acid, an ester of hyaluronic acid, an enzymatic derivative of hyaluronic acid, a cross-linked gel of hyaluronic acid, a chemically modified derivative of hyaluronic acid, or a combination thereof;

wherein the therapeutic treatment composition is in the form of a semi-solid, a liquid, a gel, a paste, a viscid liquid, a mouthrinse or in a combination of these forms, suitable for applying to a periodontal treatment site by rinsing, toothbrushing, or swabbing.

14. An oral care product according to claim 13 wherein the oral care product comprises a mouthrinse or a topically applied gel or paste.

* * * * *

UNITED STATES PATENT AND TRADEMARK OFFICE
CERTIFICATE OF CORRECTION

PATENT NO.   : 5,939,047
DATED        : August 17, 1999
INVENTOR(S)  : Jernberg

Page 1 of 1

It is certified that error appears in the above-identified patent and that said Letters Patent is hereby corrected as shown below:

Front page, [57] Abstract:
Line 4: "lease" should read --least--

Column 4:
Line 22: insert --the-- after the word "of"

Column 4:
Line 65: "suldus" should read --sulcus--

Column 5, line 15:
"periodontitig" should read --periodontitis--

Column 6:
Lines 16 and 19: "nonsteroidal" should read --non steroidal--

Column 8:
Line 51, claim 3: "nonsteroidal" should read --non-steroidal--

Signed and Sealed this

Twelfth Day of June, 2001

*Attest:*

*Attesting Officer*

NICHOLAS P. GODICI
*Acting Director of the United States Patent and Trademark Office*